US009777390B2

(12) United States Patent
Godin et al.

(10) Patent No.: US 9,777,390 B2
(45) Date of Patent: Oct. 3, 2017

(54) METHOD FOR CONTROLLING THE SIZE OF SOLID-STATE NANOPORES (71) Applicant: THE UNIVERSITY OF OTTAWA, Ottawa (CA)

(72) Inventors: Michel Godin, Ottawa (CA); Eric Beamish, Ottawa (CA); Vincent Tabard-Cossa, Ottawa (CA); Wing Hei Kwok, Ottawa (CA)

(73) Assignee: THE UNIVERSITY OF OTTAWA, Ottawa (CA)

( * ) Notice: Subject to any disclaimer, the term of this patent is extended or adjusted under 35 U.S.C. 154(b) by 358 days.

(21) Appl. No.: 14/399,091

(22) PCT Filed: May 7, 2013

(86) PCT No.: PCT/IB2013/000884
§ 371 (c)(1),
(2) Date: Nov. 5, 2014

(87) PCT Pub. No.: WO2013/167952
PCT Pub. Date: Nov. 14, 2013

(65) Prior Publication Data
US 2015/0109008 A1 Apr. 23, 2015

Related U.S. Application Data

(60) Provisional application No. 61/781,081, filed on Mar. 14, 2013, provisional application No. 61/643,651, filed on May 7, 2012.

(51) Int. Cl.
*C25F 3/14* (2006.01)
*B01D 67/00* (2006.01)
(Continued)

(52) U.S. Cl.
CPC ............... *C25F 3/14* (2013.01); *B01D 65/02* (2013.01); *B01D 67/009* (2013.01);
(Continued)

(58) Field of Classification Search
CPC ............ B81C 1/00087; B01D 67/0039; B01D 67/009; B01D 2325/02; C25F 3/14
See application file for complete search history.

(56) References Cited

U.S. PATENT DOCUMENTS

2003/0080042 A1 5/2003 Barth et al.
2005/0072689 A1 4/2005 Spohr et al.
(Continued)

FOREIGN PATENT DOCUMENTS

JP 2007186776 A 7/2007
JP 2008545518 A 12/2008
(Continued)

OTHER PUBLICATIONS

Kwok, Harold, Briggs, Kyle and Tabard-Cossa, Vincent, "Rapid fabrication of sub 5 nm solid state nanopore for low cost biosensing", Abstract submitted for the Mar. 2013 meeting of the American Physical Society, Nov. 9, 2012.
(Continued)

*Primary Examiner* — Nicholas A Smith
(74) *Attorney, Agent, or Firm* — Harness, Dickey & Pierce, P.L.C.

(57) ABSTRACT

A method is provided for precisely enlarging a nanopore formed in a membrane. The method includes: applying an electric potential across the nanopore, where the electric potential has a pulsed waveform oscillating between a high value and a low value; measuring current flowing though the nanopore while the electric potential is being applied to the nanopore at a low value; determining size of the nanopore based in part on the measured current; and removing the
(Continued)

electric potential applied to the membrane when the size of the nanopore corresponds to a desired size.

18 Claims, 7 Drawing Sheets

(51) Int. Cl.
  B01D 65/02    (2006.01)
  G01N 33/487   (2006.01)
  C25F 7/00     (2006.01)
  G01B 7/00     (2006.01)
  G01N 27/04    (2006.01)
  G01N 33/00    (2006.01)
  B81C 1/00     (2006.01)
  B82Y 15/00    (2011.01)

(52) U.S. Cl.
  CPC ........... B81C 1/00087 (2013.01); C25F 7/00 (2013.01); G01B 7/00 (2013.01); G01N 27/04 (2013.01); G01N 33/00 (2013.01); G01N 33/48721 (2013.01); *B01D 2321/22* (2013.01); *B01D 2323/42* (2013.01); *B01D 2325/02* (2013.01); *B81B 2203/0353* (2013.01); *B82Y 15/00* (2013.01); *G01N 2033/0095* (2013.01)

(56) References Cited

U.S. PATENT DOCUMENTS

| | | |
|---|---|---|
| 2007/0172386 A1 | 7/2007 | Li et al. |
| 2009/0205960 A1 | 8/2009 | Schaffer et al. |
| 2011/0174629 A1 | 7/2011 | Bouchet et al. |
| 2012/0103821 A1 | 5/2012 | Harrer et al. |
| 2014/0262820 A1 | 9/2014 | Kuan et al. |

FOREIGN PATENT DOCUMENTS

| | | |
|---|---|---|
| WO | WO-2008060324 A2 | 5/2008 |
| WO | WO-2011046706 A1 | 4/2011 |

OTHER PUBLICATIONS

International Search Report and Written Opinion of the International Searching Authority for PCT/IB2013/000884, mailed Sep. 5, 2013; ISA/CA.

International Search Report and Written Opinion of the International Searching Authority for PCT/IB2013/000891, mailed Aug. 28, 2013; ISA/CA.

M. Baklanov "Dielectric Films for Advanced Microelectronics", pp. 24-25 (2007).

J. Yota "Effects of Deposition Method of PECVD Silicon Nitride As MIM Capacitor Dielectric for GaAs HBT Technology", Sections of Experimental, and Results and Discussion; figure 8, Symposium on Silicon Nitride, (ECS) Meeting, (May 6, 2011).

METHOD FOR CONTROLLING THE SIZE OF SOLID-STATE NANOPORES

CROSS-REFERENCE TO RELATED APPLICATIONS

This application claims the benefit of U.S. Provisional Application No. 61/643,651, filed on May 7, 2012 and U.S. Provisional Application No. 61/781,081, filed on Mar. 14, 2013. The entire disclosure of each of the above applications is incorporated herein by reference.

FIELD

The present disclosure relates to a technique for tuning the size of a solid-state nanopore using high electric fields.

BACKGROUND

Biological and solid-state nanopores provide a means of sensing biomolecular analytes at the single molecule level. Individual nanopores are typically embedded in thin insulating membranes, providing the only conduit for ionic current to pass between two liquid reservoirs. Utilizing the principles of larger-scale Coulter counters, nanopore experiments relate changes in ionic current to determine the length, size, charge and conformation of charged biomolecules as they are electrophoretically driven through a nanopore in the presence of an external electric field.

While biological nanopores such as α-hemolysin typically offer greater sensitivity and low-noise properties, the supporting lipid bilayer is fragile and of fixed size, limiting their applicability. Solid-state nanopores, on the other hand, are typically fabricated in thin (10-50 nm) insulating membranes, such as silicon nitride or silicon oxide membranes, and can be made of different sizes, be readily integrated with wafer-scale technologies, and are more robust, allowing for a wider range of experimental conditions. Despite these advantages, solid-state nanopore technologies suffer from several practical drawbacks that limit their usefulness for biomolecular studies. While control of nanopore size is possible, it is typically expensive and laborious to achieve, requiring specialized equipment and skilled personnel. For example, nanopores drilled by focused-ion beam have been recently shown to shrink under specific experimental conditions in a scanning electron microscope (SEM). In other approaches, nanopores drilled by transmission electron microscopy (TEM) can expand or shrink depending on the beam conditions and subsequent exposure to aqueous solvents. In these cases, the achievable range of nanopore sizes is limited, difficult to control and even unreliable as the size of the nanopore can change following chemical treatment or when immersed in a particular liquid environment.

The ionic current through solid-state nanopores can also suffer from a high degree of noise, the sources of which are an intensely investigated topic in nanopore literature. While various methods have been proposed to reduce electrical noise, the yield of reliable, stable low-noise nanopores is typically still quite low. Deposition of carbonaceous residues during drilling and imaging can have detrimental effects on the electrical signal quality, often making complete wetting a challenge and causing the formation of nanobubbles that can be difficult to remove. Furthermore, clogging of the nanopore by analyte molecules degrades signal quality rendering pores unusable for further experiment. These effects greatly reduce yield of functional nanopore devices and increase the cost associated with solid-state nanopore research. Thus, reproducible fabrication and tuning of reliable nanopores remains a challenge not only for the academic research environment but for the commercialization of any nanopore-based technology.

This section provides background information related to the present disclosure which is not necessarily prior art.

SUMMARY

This section provides a general summary of the disclosure, and is not a comprehensive disclosure of its full scope or all of its features.

A method is provided for tuning a nanopore formed in a solid-state membrane. The method includes: applying an electric potential across the nanopore, where the electric potential has a pulsed waveform oscillating between a high value and a low value; measuring current flowing through the nanopore; determining size of the nanopore based in part on the measured current; and removing the electric potential applied across the nanopore when the size of the nanopore corresponds to a desired size.

In one aspect of the disclosure, measuring of the current flowing through the nanopore occurs while the electric potential is being applied at a high value; whereas, in another aspect, measuring of the current flowing through the nanopore occurs while the electric potential is being applied at a low value.

In one aspect of the disclosure, the method is further defined to include: selecting a value for an electric potential that induces an electric field in a nanopore and applying the electric potential for a predetermined period of time, where the electric field is approximately 0.3 volts per nanometer. After the predetermined time period, the electric potential applied across the nanopore is reduced to a value less than the selected value and the current flowing though the nanopore is measured while the electric potential is applied at the reduced value. The size of the nanopore is determined based in part on the measured current.

In some aspects of the disclosure, this process is repeated until the measured current exceeds a threshold. When reapplying relatively high electric potential, the polarity of the electric potential may be reversed to achieve or maintain symmetry in pore geometry. Once the measured current exceeds the threshold, the electric potential is removed.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
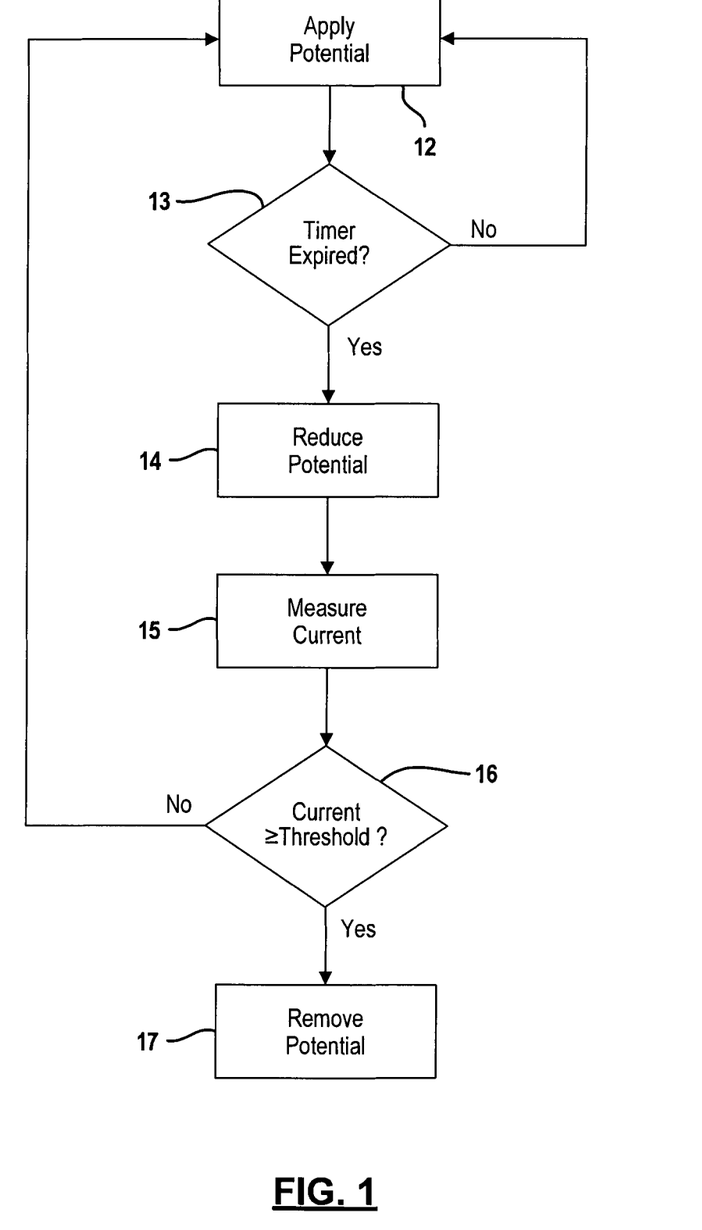
FIG. 1 is a flowchart depicting an example technique for tuning the size of a nanopore.

FIG. 1 illustrates an example technique for tuning the size of a nanopore pre-formed in a membrane. The application of high electric fields is used to precisely enlarge the size of the nanopores while ensuring optimal low-noise performance. High electric fields are produced as indicated at 12 by applying an electric potential across the nanopore. The value of the electric potential is selected to induce an electric field that is above 0.1 volts per nanometer (typically between 0.1 and 0.4 volts per nanometer). While particular values are provided above, the induced electric field will vary depending upon membrane material and other factors but exceeds the Ohmic range of the nanopore being conditioned (typically above 0.1 volts per nanometer).

Prolonged exposure to high electric fields initiates the removal of the membrane material constituting the pore wall, resulting in an increase in nanopore diameter. This growth can be precisely controlled by tuning the strength and duration of the electric field. The relatively high electric potential is applied across the nanopore for a predetermined period of time as indicated at 13. In one embodiment, the time period falls within the range of 100 milliseconds to 5 seconds. In other embodiments, the time period may be much smaller (e.g., a few microseconds) or much longer (e.g., a few minutes). After the time period expires, the electric potential applied across the nanopore is reduced at 14 to a value less than the relatively high value. For example, the electric potential may be reduced to a value which induces an electric field in the range of zero to 0.1 volts per nanometer.

While the reduced electric potential is applied across the nanopore, the current flowing through the nanopore is measured at 15, where the measured current correlates to the size of the nanopore as further explained below. In some embodiments, the electric potential is applied as a series of pulses with a measurement between each pulse. In other embodiments, the current measurement following a group of pulses (e.g., after every n pulses, where n is greater than 1).

In an alternative approach, the current flowing through the nanopore is measured while the applied electric potential remains high. The measured current provides a less accurate estimate of the nanopore size as the electric field is above the Ohmic range of the nanopore system. Thus, as the size of the nanopore approaches the desired size, the electric potential is applied in a pulsed manner as described above, such that the current is measured at the reduced electric potential.

When the size of the nanopore is equivalent to a desired size, the electric potential applied to the nanopore is removed. In an example embodiment, the size of the nanopore is determined by comparing 16 the measured current to a threshold current, where the threshold current is selected to correspond to the desired size. The electric potential is removed at 17 when the measured current is equal to or exceeds the threshold; otherwise, the process of applying a high enlarging potential followed by a lower measurement potential is then repeated until this condition is met. Through the cyclic application of relatively high voltage pulses, a clean, low-noise nanopore surface ideal for single-molecule studies is produced. As current traces degrade over the course of an experiment due to clogging of the nanopore as molecules adsorb to the nanopore surface, this process can be repeated to recover clogged devices that would have otherwise been discarded. As such, the yield of functional nanopores is further increased by the ability to use the same device multiple times. This technique provides several advantages as it is rapidly performed in liquid under experimental conditions, requires only standard laboratory equipment, can be automated with software, and produces functional high-quality nanopores with a yield of over 95%.

Although membranes having different thicknesses fall within the scope of this disclosure, the nanopores studied in this disclosure were drilled in 30-nm or 10-nm thick silicon nitride membranes. Membranes comprised of other dielectric materials (e.g., other oxides and nitrides), which are commonly used as gate materials for transistors, also fall within the scope of this disclosure. Likewise, membranes may be comprised of other materials such as graphene, boron nitride and the like.

While the protocol described here can be applied to solid-state nanopores of various materials fabricated using any method, they are commonly drilled by TEM using previously established protocols. The nanopores used for the experiments described here are drilled by TEM and are typically between 4-nm to 10-nm in diameter. While both 30-nm and 10-nm thick membranes were mounted and conditioned using the protocol set forth below, voltage biases described here refer to those required for 30-nm thick membranes unless otherwise stated. For membranes with different thicknesses, the applied voltage should be adjusted accordingly to generate an electric field in the range of 0.1-0.4 volt per nanometer (above the Ohmic limit) inside the nanopore.

Once a nanopore exists in an insulating membrane, it can be directly mounted in the liquid cell without further processing or cleaning. However, if it is necessary to remove traces of contaminants between experiments, or in some cases of severe clogging, nanopore chips can be cleaned using either piranha solution (3:1 $H_2SO_4$:$H_2O_2$) or by exposure to oxygen plasma. This process can also be used to remove any contamination left over from the drilling, imaging and handling processes rendering the nanopore surface hydrophilic to aid in wetting or to remove a particularly persistent clog. Nevertheless, most devices could be reconditioned upon clogging in situ, using the method described herein, consequently reducing preparation time and the need to deal with harsh chemicals.

Figure 2:
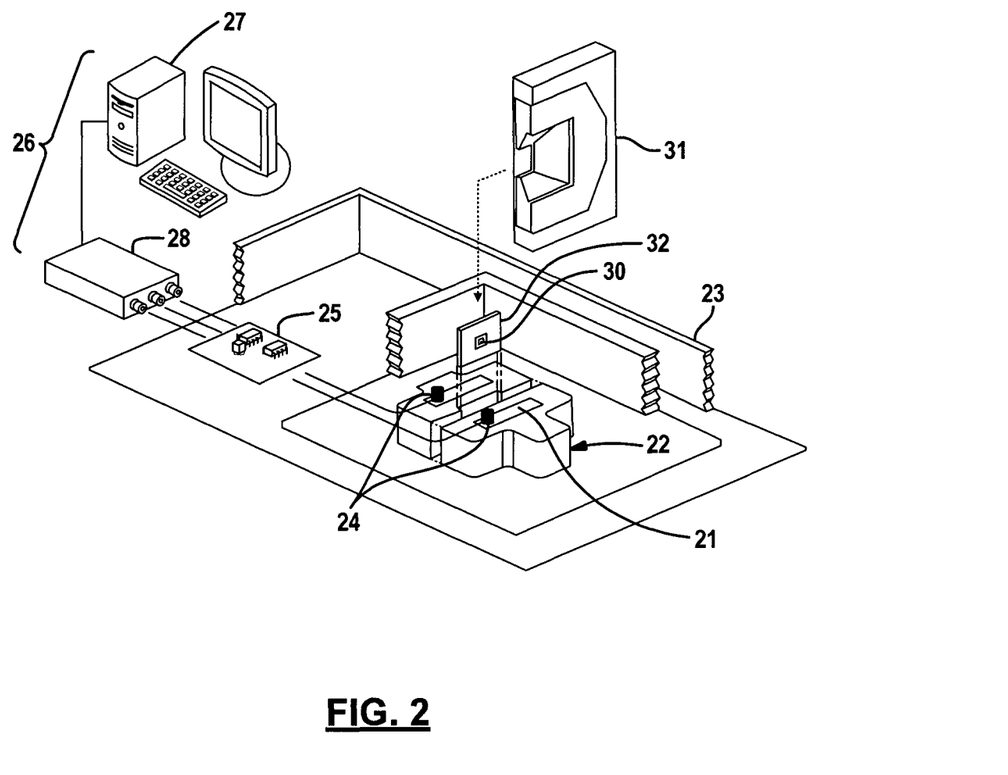
FIG. 2 is a diagram depicting an example setup for tuning nanopores.

FIG. 2 depicts an example setup for tuning nanopores pre-formed in a membrane. The setup is comprised generally of a fluidic cell 22; a pair of electrodes 24 (e.g., Ag/AgCl) electrically coupled to a current amplifier circuit 25; and a controller 26 interfaced with the current amplifier circuit 25. The fluidic cell 22 is further defined by two reservoirs 21 fluidly coupled via a passageway to each other, with the nanopore itself acting as the only conduit for ionic current between the two reservoirs. The reservoirs can be filled with an aqueous solution (e.g., chloride-based salt), a non-aqueous solution (e.g., LiCl in ethanol) or other types of ionic solutions.

The current amplifier circuit 25 operates to create a potential between the electrodes and measure the current flow through the nanopore. In some embodiments, the controller 26 may be implemented by a data acquisition circuit 28 coupled to a personal computer 27 or another type of computing device. Thus, the setup is similar to what is commonly used for biomolecular detection. Other setups for tuning a nanopore are contemplated by this disclosure.

In the example setup, a nanopore cell 22 is used to house a silicon chip 32 which in turn houses the membrane 30 containing a nanopore. An example protocol for mounting the silicon chip 32 in the setup is as follows. Clean the nanopore cell 22 by placing it in 20% nitric acid solution and boiling for 10 minutes. Carefully remove the cell 22 from nitric acid and place it in boiling de-ionized water for 10 minutes. Remove the cell 22 and further boil in fresh de-ionized water for an additional 10 minutes to ensure complete removal of nitric acid. Remove the beaker from the hot plate and allow it to cool to room temperature. Remove the cell 22 from the beaker and blow dry with filtered air or $N_2$. Store the cell 22 in a clean Petri dish. Degas filtered, buffered electrolyte solution by placing under vacuum in a sonicator for 30 minutes at 40° C. While various salt solutions of different pHs can be used for nanopore conditioning and enlarging, the majority of the experiments described here are performed in 1M KCl solution buffered with HEPES at pH 8. Clean two silicone elastomer gaskets for the silicon chip 32 by sonicating in ethanol for at least 10 minutes. Place the chip 32 on a clean elastomer gasket being careful to align the membrane window with the gasket opening. Place and align a second gasket atop the chip 32. Place the chip 32 and gaskets on the reservoir inlet of one half of the cleaned nanopore cell 22. Assemble the cell 22 by screwing the other half in place. Wet the chip 32 by pipetting ethanol into the cell reservoirs and placing in a vacuum chamber until a few bubbles are seen to exit the inlets. Remove ethanol by flushing the reservoirs with at least 3 ml degassed filtered electrolyte solution. Take care to remove overflow using an aspirator. The silicone chip 32 is then mounted between the two reservoirs 21 of the fluidic cell 22. It is readily understood that one or more of these steps may be optional depending on the circumstances. Moreover, other techniques for mounting the membrane containing a nanopore in the setup also fall within the scope of this disclosure.

Before tuning, the nanopore may optionally be characterized. To do so, place the nanopore cell in the electrically shielded experimental setup 23 and place the electrodes 24 in each reservoir. This setup is similar to that shown in FIG. 2 with the exception of the current amplifier circuit and controller is replaced with a low-noise resistive feedback amplifier (e.g., an Axopatch 200B patch clamp amplifier from Molecular Devices Inc). Using the amplifier in voltage-clamp mode, apply potentials sweeping from −200 mV to +200 mV and record the I-V (current-to-voltage) characteristics. Fit the I-V curve to obtain nanopore conductance, which can be used to calculate its diameter in solution. If the calculated diameter is much smaller than expected from TEM imaging, the pore is likely not completely wetted and/or contains debris or contamination. Apply a 200 mV potential across the nanopore and record the ionic current for 30 seconds. Perform a power spectral density (PSD) analysis, of the ionic current and integrate to quantify the electrical noise characteristics of the nanopore. If the noise is above 15 pA RMS at 5 kHz bandwidth, then the pore is likely not completely wetted and/or contains contamination and cannot be reliably used in experiment.

If the I-V curve generated exhibited asymmetry or less-than-expected conductance, or the current trace showed instability and high noise levels at low-frequencies (<10 kHz), it is necessary to condition the nanopore with high electric fields to remove any contamination on the nanopore surface and/or wet the nanopore. While this method does not affect the high-frequency noise caused by the membrane capacitance or any parasitic capacitance coupled to the input of the current amplifier used in measurements, low-frequency noise (also called 1/f noise) can be greatly reduced. It is readily understood that such conditioning is not needed in some instances.

FIG. 2 is an example setup which may be used to perform this conditioning. To do so, disconnect the electrodes from the patch-clamp amplifier. Connect one of the electrodes to a computer-controlled power supply capable of generating greater than 3 volts (>0.1 V/nm electric field strength for the 30-nm thick membranes used here) and the other to the current amplifier circuit 25 that can be monitored in real time. Apply a potential difference of 400 mV (measurement voltage) across the nanopore for at least 5 seconds. Calculate the mean current value from the final 1 second of data to determine the conductance of the nanopore. Calculate the diameter of the nanopore based on this conductance, which can be done automatically using software implemented by the controller 26 and the nanopore conductance model of choice based on the most likely geometry. It should correspond to the diameter measured from the I-V curve. Apply a 200 ms pulse of 6 volts (wetting voltage) across the nanopore to produce an electric field of 0.2 V/nm followed by a 5 second measurement period at 400 mV. Again, calculate a diameter of the nanopore using the final 1 second of data and compare with the value expected from TEM measurements to ensure that the nanopore is fully wet. Alternatively, ramping the voltage from −200 mV to +200 mV and fitting an I-V curve as described above can be done at this stage to provide a more precise estimate nanopore conductance and thus size. This process of applying high electric field pulses with increasing voltage can be repeated until the current signal during the measurement period is stable and showing the expected conductance. It is not recommended to exceed 10 volts (i.e. >0.3 V/nm) at this stage, as this may enlarge or damage the nanopore rapidly and/or uncontrollably.

The diameter of the nanopore is crucial in determining its functionality for a particular biomolecular sensing application. To this end, a pre-formed nanopore can be enlarged to a desired size by applying high electric fields until the appropriate diameter is achieved with the same setup used to clean and wet the nanopore (i.e., FIG. 2). Using the same setup, apply a 200-500 mV bias across the pore to obtain a diameter measurement. While less precise than fitting an I-V curve, a single point measurement can be used to roughly estimate the nanopore size rapidly.

An electric potential having a pulsed waveform is applied across the nanopore (e.g., 2 second pulse of 8 volts across the nanopore followed by a measurement period of about 5 seconds at 400 mV). Calculation of the new diameter will typically show a very small increase in nanopore size (i.e., <0.1 nm). Repeat this process cyclically, alternating between enlargement and measurement voltages to obtain in situ and real-time measurements of increasing nanopore diameter. If faster growth rate is desirable, the magnitude of the voltage applied can be increased incrementally up to 10 volts. Growth will typically accelerate as the pore enlarges with the rate of increase in conductance ranging from 0.03 nSs$^{-1}$ to 10 nSs$^{-1}$, depending on the size of the nanopore, strength of the electric field and electrolyte solution properties. As such, the ionic strength and pH of the electrolyte solution can also be varied to control nanopore growth rate.

When the desired diameter is reached, stop the application of high electric fields. This tuning technique can be implemented automatically using a computer program implemented by the controller 26. Reconnect the patch-clamp amplifier to the electrodes. Acquire new, low-noise I-V and current trace data at 200 mV to confirm the diameter of the nanopore and verify low-noise current signals as in the steps noted above. If necessary, repeat conditioning and enlarging protocol.

Figure 3A:
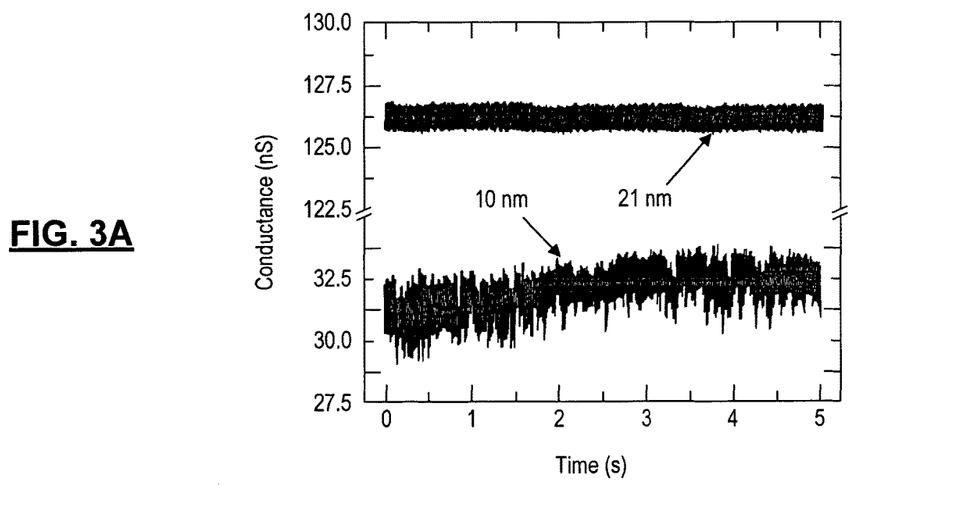
FIGS. 3A and 3B are graphs illustrating current traces before and after application of high electric fields, respectively.
Figure 3B:
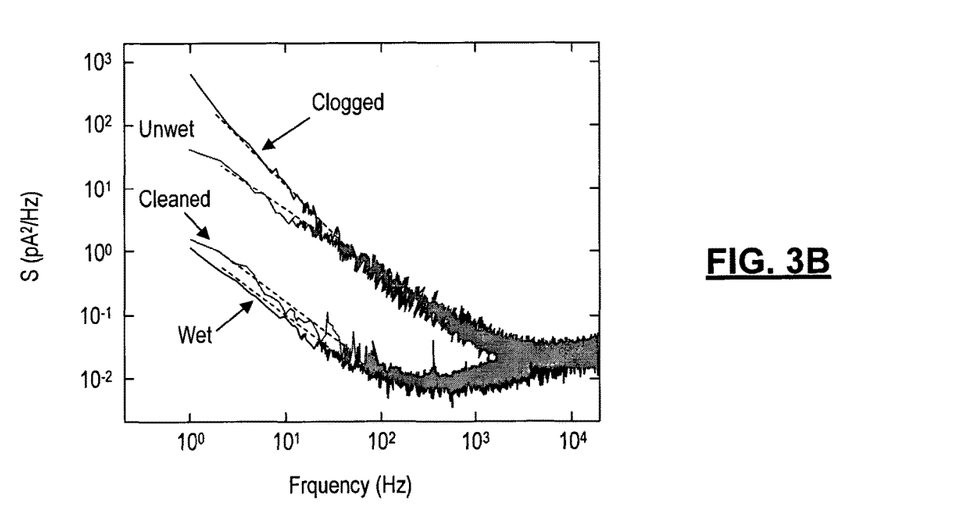

FIG. 3A shows two typical ionic current traces of a 10-nm nanopore in a 30-nm thick membrane before and after treatment with high electric fields. Upon mounting a newly drilled nanopore, the likelihood of obtaining an unstable and noisy ionic current signal, exhibiting a high degree of low-frequency fluctuation, is usually high. The nanopore shown in FIG. 3A highlights this behaviour. Its conductance is considerably less than expected for a nanopore of its size, most likely due to incomplete wetting. Upon the application of high electric fields of 0.27 V/nm in magnitude produced by 8 V pulses (90 pulses of 2 second duration), the nanopore becomes fully wet. It is subsequently enlarged to 21 nm in diameter. At this point, the pore exhibits a stable conductance with low-noise properties. Quantitative analysis of noise in similar nanopores is shown as power spectral density plots in FIG. 3B. The low-frequency noise amplitude of unwet and/or clogged pores is very high (>20 pA RMS for a 5 kHz bandwidth), rendering them unusable in experiment. Upon conditioning with high electric fields, noise power at low frequencies (<10 kHz) is diminished by up to 3 orders of magnitude and ready for low-noise experiments.

Figure 4A:
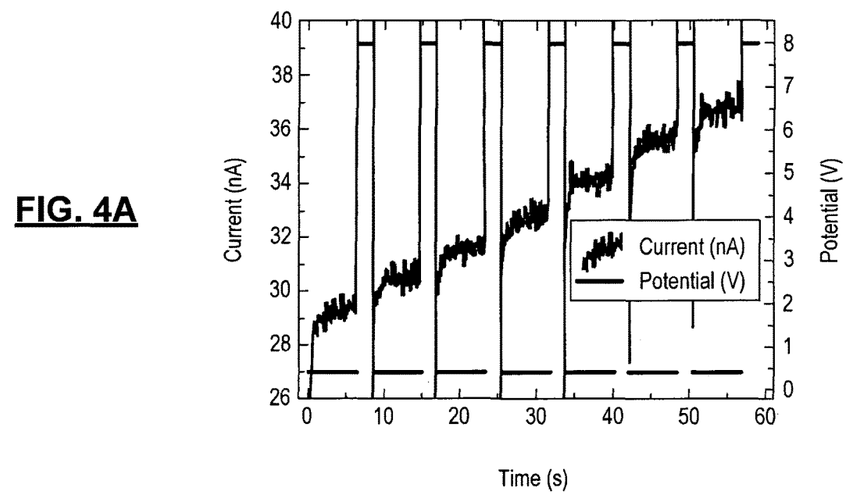
FIG. 4A is a graph illustrating the pulsed waveform of the electric potential applied across the nanopore, and the increasing ionic current through the nanopore indicating growth.

FIG. 4A shows a typical current measurement as the potential applied is pulsed between high electric fields for enlarging and low electric field measurement periods. In this example embodiment, the potential is applied as a series of square waves. In some embodiments, the electric potential for a given pulse may be ramped up or down (e.g., linearly, exponentially, gradually, etc.) to or from a peak value. In other embodiments, the electric potential may vary at the peak value (e.g., sinusoidal shape). Other types of waveforms for applying the electric potential across are contemplated by this disclosure.

After each subsequent pulse, the resultant ionic current through the nanopore at the measurement voltage (i.e. the nanopore conductance) increases by a finite amount. This demonstrates that the nanopore is increased in size, as the diameter d can be inferred from its conductance G in a solution of conductivity σ, approximating the nanopore as having cylindrical geometry of effective length $l_{eff}$. While various other models exist for relating nanopore conductance to its geometry, the following relation has been validated for TEM-drilled nanopores, in high salt concentrations, over a wide range of diameters of interest for biomolecular translocation.

$$G = \sigma \left[ \frac{4 l_{eff}}{\pi d^2} + \frac{1}{d} \right]^{-1}$$

Figure 5:
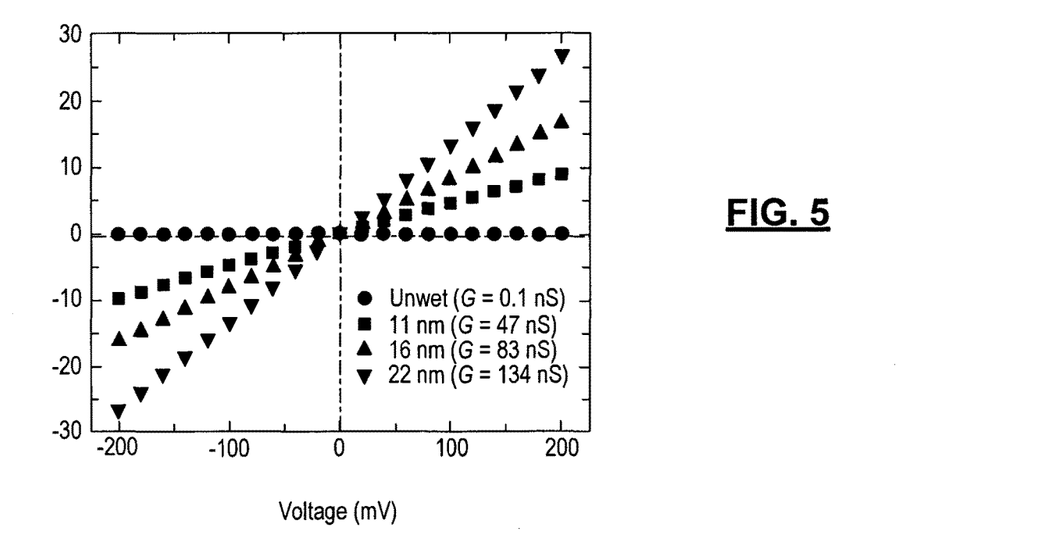
FIG. 5 is a graph illustrating I-V measurements of conductance which confirm that the nanopore sizes have increased.

Once the desired diameter is reached, the process is automatically stopped by the software. The resulting nanopore diameter can then be confirmed using precise I-V measurements, as shown in FIG. 5. It is important to note that nanopores treated using high electric fields are fully functional.

In one aspect of this disclosure, the polarity of the electric potential may be reversed for alternating pulses in order to achieve or maintain symmetry in pore geometry. Additionally, the measurement period can be extended or modified to perform an in situ I-V measurement to obtain more accurate nanopore sizes or noise properties.

Figure 4B:
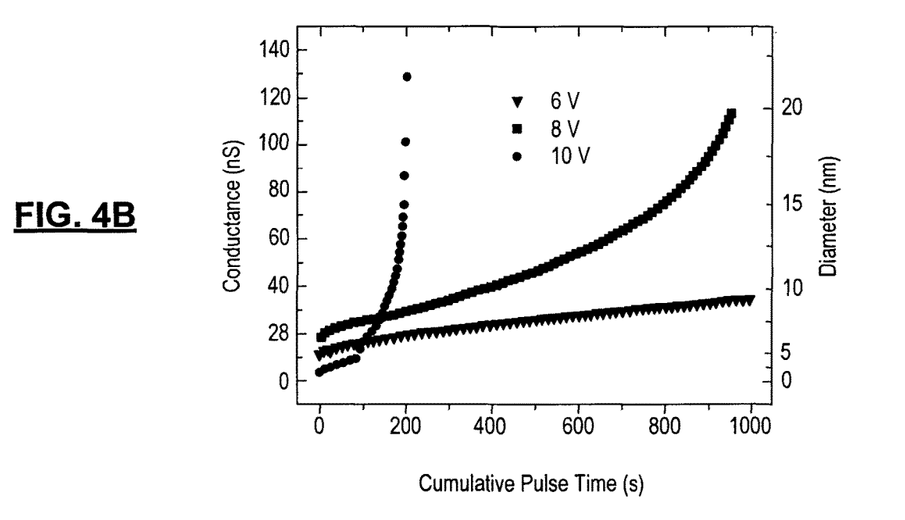
FIG. 4B is a graph illustrating that growth rate can be controlled by varying the applied potential.
Figure 4C:
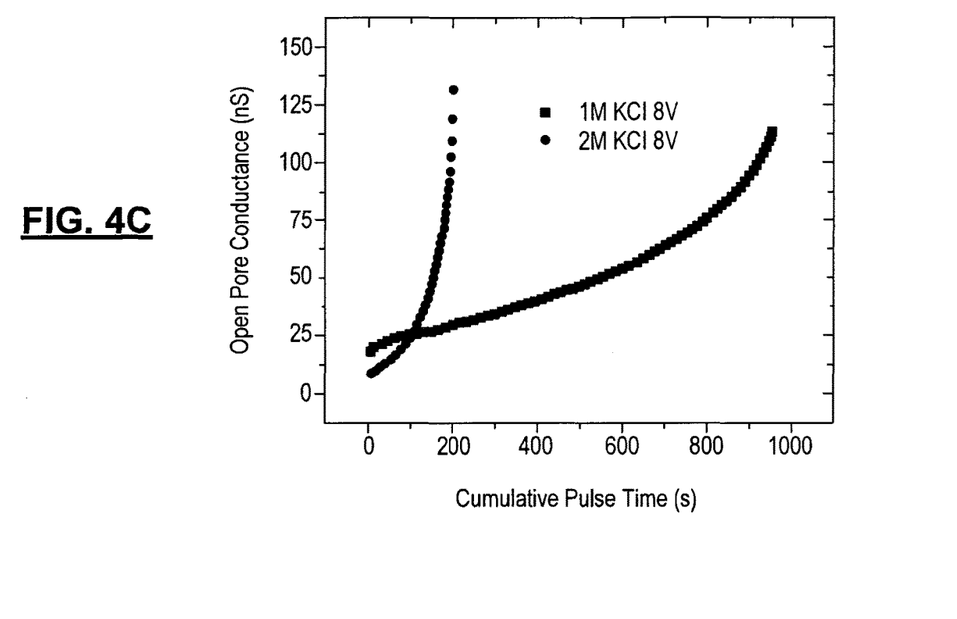
FIG. 4C is a graph illustrating that growth rate can be controlled by varying ionic strength of solution.

Various factors may affect the growth rate of the nanopore. For example, increasing the magnitude of the applied voltage can increase the growth rate of the nanopore as shown in FIG. 4B. Varying the ionic strength of the ionic solution can also increase the growth rate of the nanopore as shown in FIG. 4C. Other factors affecting the growth rate include but are not limited to temperature, pH of the ionic solution, salt species of the solution, etc.

Treatment using high electric fields prepares solid-state nanopores for biomolecular experiments by providing the ability to precisely control the size of the nanopore while ensuring minimal noise in the ionic current measurements. This approach is further validated by performing biomolecular translocation experiments on λ DNA (48.5 kbp double-stranded). A control experiment is done by acquiring current traces under an applied potential of +150 to +300 mV in the absence of any sample to verify that no current blockades are detected after 2 minutes. Add DNA to the cis reservoir for a final concentration of 0.5-5 ng/μL. Reflux gently by pipette for at least 10 seconds to ensure homogeneous distribution of the sample throughout the reservoir. For a 30-nm thick nanopore, apply a potential bias of +150 to +300 mV to the trans reservoir and measure the ionic current passing through the nanopore. For very short translocation events, it is desirable to sample at a high frequency (250 kHz or greater) with a relatively high low-pass filtering frequency (100 kHz). Monitor the ionic current using software to detect transient current blockades as molecules translocate through the nanopore. The ionic current traces of molecular translocation can be analyzed to determine blockage depth, duration and frequency to infer information about the sample of interest. Conversely, if information about the translocating molecules is known, this data can be used to investigate properties of the nanopore itself.

Figure 6:
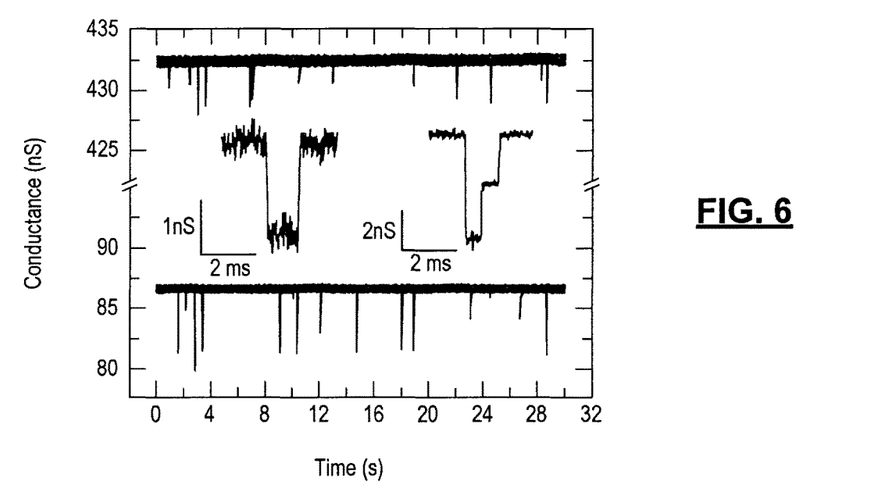
FIG. 6 is a graph illustrating current traces associated with translocation of DNA molecules.
Figure 7A:
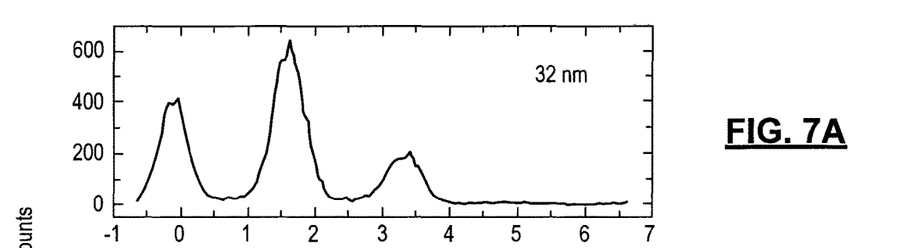
FIGS. 7A and 7B are histograms of the current blockage during translocation events for 11 nm and 32 nm pores, respectively.
Figure 7B:
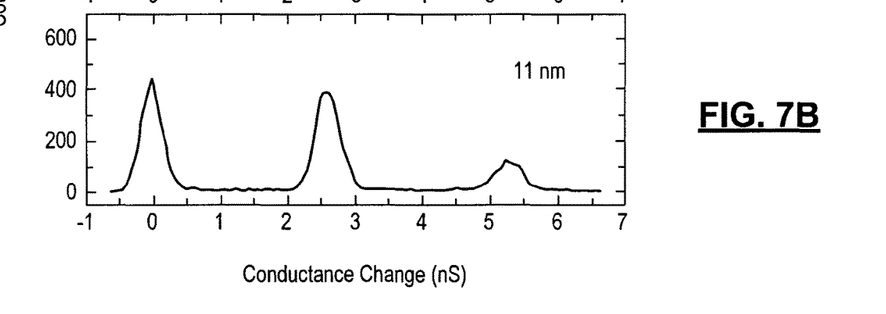

FIG. 6 shows current traces associated with the translocation of λ DNA molecules. In this figure, dsDNA is driven through two nanopores that were enlarged to 11-nm and 32-nm using the method described above. In each case, the baseline current is extremely stable and clear current blockades are observed as dsDNA molecules translocate through the nanopore, displaying high signal-to-noise single-molecule translocation events. As shown in the insets of FIG. 6, multiple discreet blockage levels are observed as individual folded molecules translocate, as expected for nanopores of these sizes. Histograms of the current blockage amplitude during translocation events through each pore are shown in FIGS. 7A and 7B. The low-noise properties of the nanopores reveal distinct, easily resolvable peaks corresponding to the baseline (no DNA), single (one DNA strand—unfolded) and double blockage states (two DNA strands—folded). Of note is the fact that the absolute current blockade corresponding to a single dsDNA molecule occupying the pore is different for the large and small nanopores. This provides indirect evidence that the application of high electric fields is in fact enlarging existing nanopores, as the same current blockage amplitude would be observed if other pores or cracks were being created in the membrane during the process.

Figure 8:
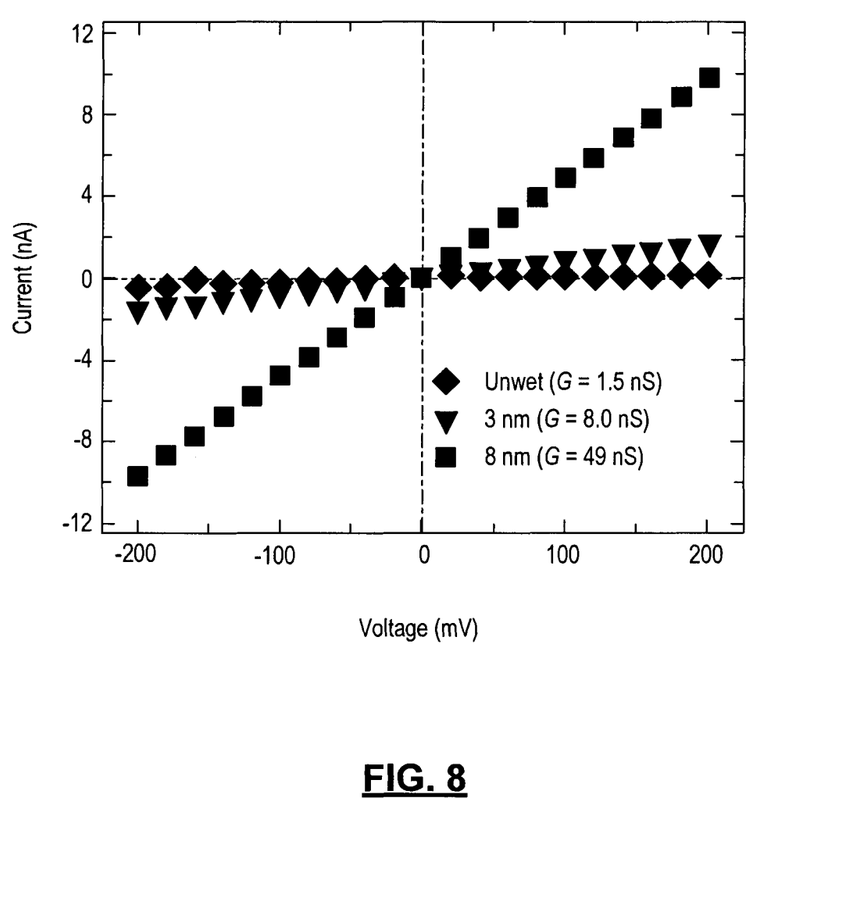
FIG. 8 is a graph illustrating the effectiveness of enlarging nanopores under different conditions. In this case, the membrane thickness was 10 nm.

Similarly, FIG. 8 illustrates the effectiveness of high electric fields for enlarging nanopores fabricated in membranes of different thickness. Here, a nanopore created in a 10-nm $SiN_x$ membrane is enlarged. Upon the application of alternating ±3 V (±0.3 volts per nanometer) pulses of 4 second duration (30 total), the nanopore becomes wet and exhibits ideal I-V characteristics for a 3 nanometer pore. The methodology was then repeated for 400 subsequent pulses and the nanopore was enlarged to 8 nanometers. This enlargement, performed at comparable electric fields but lower applied voltage bias than for nanopores fabricated in 30-nm membranes, shows that the process is in part electric field driven. As the current blockade produced by translocation through a thinner membrane is larger than that produced in thicker pores, nanopores in thin membranes treated in this fashion can be used to study shorter molecules such as proteins with increased sensitivity.

Control of nanopore size is of fundamental importance in biomolecular sensing applications. Nanopore diameters must be on the order of the size of the molecules being probed; they must be large enough to accommodate the sample but small enough to achieve optimal signal-to-noise. While the control of size using the method presented of applying high electric fields is unidirectional in that nanopore diameters are only increased throughout the process, nanopores with diameters between 3-100 nm can be fashioned with sub-nanometer precision. As 3-4 nm pores can be readily fabricated using a TEM or other methods, this allows for the reliable fabrication of solid-state nanopores for a wide range of applications from probing ssDNA structure to the interaction of bulky protein-ligand complexes. While nanopore growth above 100 nm can be faster and less precise, more moderate enlarging conditions can be employed to achieve better control over the process. As such, the most important step for achieving effective size control is the choice of pulse strength and duration in order to balance enlarging efficiency and the level of precision required in achieving a desired pore diameter. Depending on the final size, it is generally possible to enlarge a nanopore to sub-100-nm diameters in a few minutes.

Similarly, large low-frequency current fluctuations preclude single-molecule studies as it is nearly impossible to differentiate translocation signals from background noise. Incomplete wetting, the presence of carbonaceous residues remaining after initial fabrication and adsorption of debris on the nanopore wall can degrade signal quality, requiring additional cleaning with harsh chemical treatments that are often inefficacious. Interestingly, it is common for solid-state nanopore protocols to emphasize the importance of cleaning the nanopore before mounting to aid wetting, and the suggested solution for failed attempts is to perform additional piranha or plasma cleaning which can be extremely time consuming. With the application of high electric fields, these lengthy protocols may not be necessary depending on the experiment to be performed, and the most important steps in mitigating electrical noise is a simple increase in voltage and/or pulse duration to completely wet the pore and remove loosely-bound debris. Nanopores treated in this fashion can reliably be used in biomolecule translocation experiments, such as the passage of DNA and proteins. If these molecules adhere to the pore wall leading to a clogged and noisy electrical signal, high electric field pulses can be reapplied to remove the obstruction and regain low-noise properties for further experimentation, without unmounting of the nanopore chip from the fluidic cell.

The application of high electric fields using the setup described is currently limited by the requirement of an external power supply that can apply up to 10 V and current amplifier, which lack the sensitivity and low-noise properties at high-bandwidth (>1 kHz) for single molecule sensing. While typical biomolecular experiments rely on a low-noise current amplifier that is limited to ±1 V (such as the Axopatch 200B), it is straightforward to design a single system that could accomplish both high electric field conditioning and sensitive current measurement with an adjustable gain. Despite this limitation, the transition from one setup to the other is quick and straightforward. In comparison with existing techniques for controlling nanopore size such as the use of SEM, thermal oxidation and membrane reshaping, high electric fields offer a faster, more precise and less expensive methodology that can be performed on the lab bench using standard equipment and provide a broader range of nanopore sizes. Furthermore, the process is performed in situ under experimental conditions, improving the reliability and precision of nanopore size control. Moreover, the ability to rapidly and reproducibly reduce low-frequency noise, and to subsequently enlarge a nanopore to a desired size, also make the preparation of nanopores more reliable and prolongs the lifetime of solid-state nanopores, as previously used pores can be rejuvenated and reconditioned for further experiments. Over 95% of nanopores of varying thicknesses conditioned with high electric fields in our laboratory exhibited very little low-frequency noise characteristic, rendering them suitable for biomolecule sensing. These procedures allow for experiments to be more accessible to researchers and potentially allowing for a path towards commercialization of nanopore technologies through more robust fabrication processes.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for precisely enlarging the size of a nanopore formed in a membrane, comprising:
   a) selecting a value for an electric potential that induces an electric field in a nanopore, where the electric field is above 0.1 volts per nanometer;
   b) removing material of the membrane to enlarge the nanopore by applying, for a predetermined period of time, an electric potential at the selected value across the nanopore disposed in an ionic solution;
   c) after the predetermined time period, reducing the electric potential applied across the nanopore to a value less than the selected value;
   d) measuring current flowing though the nanopore, while the electric potential is applied at the reduced value; and
   e) determining size of the nanopore based in part on the measured current.

2. The method of claim 1 wherein determining size of the nanopore further comprises removing the electric potential applied across the nanopore when the measured current is equal to or exceeds a threshold.

3. The method of claim 1 further comprises
   f) increasing the electric potential applied across the nanopore to the selected value when the measured current is less than a threshold and
   g) repeating steps (b)-(f) until the measured current is equal to or exceeds the threshold.

4. The method of claim 1 further comprises selecting the value of the electric potential such that the electric field is approximately 0.3 volts per nanometer.

5. The method of claim 1 further comprises selecting the value of the electric potential such that the electric field falls within a range of 0.10 volt per nanometer to 0.4 volts per nanometer.

6. The method of claim 1 further comprises applying the electric potential at the reduced value for period of time that enables ohmic ionic current to stabilize.

7. The method of claim 2 wherein determining size of the nanopore further comprises reapplying the electrical potential at the selected value across the nanopore when the measured current is less than the threshold, where polarity of the electric potential is reversed.

8. The method of claim 1 wherein applying an electric potential further comprises increasing the value of the electric potential to increase growth rate of the nanopore.

9. The method of claim 1 wherein applying an electric potential further comprises increasing ionic strength of the ionic solution to increase growth rate of the nanopore.

10. A method for precisely enlarging size of a nanopore formed in a membrane, comprising:
   applying an electric potential across the nanopore disposed in an ionic solution, the electric potential having a pulsed waveform oscillating between a high value and a low value and induces an electric field in the nanopore;
   measuring current flowing though the nanopore while the electric potential is being applied across the nanopore at the low value;
   determining size of the nanopore based in part on the measured current; and
   removing the electric potential applied to the nanopore when the size of the nanopore corresponds to a desired size.

11. The method of claim 10 further comprises selecting the high value for the electric potential such that the electric field falls within a range of 0.1 volt per nanometer to 0.4 volts per nanometer.

12. The method of claim 10 further comprises selecting the low value for the electric potential such that the electric field is below 0.1 volts per nanometer.

13. The method of claim 10 wherein removing the electric potential includes comparing the measured current to a threshold and removing the electric potential from across the nanopore when the measured current exceeds the threshold.

14. The method of claim 10 wherein applying an electric potential further comprises alternating polarity of the high value between a positive value and a negative value for every other pulse.

15. A method for enlarging size of a nanopore formed in a membrane, comprising:
   selecting a value for an electric potential that induces an electric field in a nanopore, where the electric field is above 0.1 volts per nanometer;
   removing material of the membrane to enlarge the nanopore by applying an electric potential at the selected value across the nanopore disposed in an ionic solution;
   measuring current flowing through the nanopore while the electric potential is applied across the nanopore;
   estimating size of the nanopore based in part on the measured current; and
   removing the electric potential applied across the nanopore when the measured current exceeds a threshold.

16. The method of claim 15 further comprises
   reducing the electric potential applied across the nanopore to a value less than the selected value;
   measuring current flowing through the nanopore while the electric potential is applied at the reduce value; and
   determining the size of the nanopore based in part on the current measure while the electric potential is applied at the reduced value.

17. The method of claim 15 further comprises selecting the value of the electric potential such that the electric field is approximately 0.3 volts per nanometer.

18. The method of claim 15 further comprises selecting the value of the electric potential such that the electric field falls within a range of 0.10 volt per nanometer to 0.4 volts per nanometer.

* * * * *